(12) United States Patent
Paufique

(10) Patent No.: US 9,138,400 B2
(45) Date of Patent: Sep. 22, 2015

(54) COSMETIC USE OF SKIN CELL AUTOPHAGY ACTIVATORS

(75) Inventor: Jean Paufique, Objat (FR)

(73) Assignee: SOCIETE INDUSTRIELLE LIMOUSINE D'APPLICATION BIOLOGIQUE DITE SILAB, Objat (FR)

( * ) Notice: Subject to any disclaimer, the term of this patent is extended or adjusted under 35 U.S.C. 154(b) by 562 days.

(21) Appl. No.: 13/473,174

(22) Filed: May 16, 2012

(65) Prior Publication Data

US 2012/0225092 A1     Sep. 6, 2012

Related U.S. Application Data

(62) Division of application No. 13/133,046, filed as application No. PCT/FR2009/052410 on Dec. 4, 2009, now Pat. No. 8,512,764.

(30) Foreign Application Priority Data

Dec. 5, 2008   (FR) ..................................... 08 58308

(51) Int. Cl.

| A61K 36/00 | (2006.01) |
|---|---|
| A61K 36/06 | (2006.01) |
| A61K 36/02 | (2006.01) |
| A61K 36/752 | (2006.01) |
| A61K 8/97 | (2006.01) |
| A61K 8/99 | (2006.01) |
| A61K 36/04 | (2006.01) |
| A61K 36/062 | (2006.01) |
| A61K 36/185 | (2006.01) |
| A61K 36/42 | (2006.01) |
| A61K 36/48 | (2006.01) |
| A61Q 19/08 | (2006.01) |

(52) U.S. Cl.
CPC ... *A61K 8/97* (2013.01); *A61K 8/99* (2013.01); *A61K 36/04* (2013.01); *A61K 36/062* (2013.01); *A61K 36/185* (2013.01); *A61K 36/42* (2013.01); *A61K 36/48* (2013.01); *A61K 36/752* (2013.01); *A61Q 19/08* (2013.01)

(58) Field of Classification Search
None
See application file for complete search history.

(56) References Cited

U.S. PATENT DOCUMENTS

| 5,591,429 A | 1/1997 | Wilson et al. |
|---|---|---|
| 2005/0048008 A1 | 3/2005 | Gupta |
| 2005/0058672 A1 | 3/2005 | Gupta |
| 2005/0191267 A1 | 9/2005 | Luanratana |

FOREIGN PATENT DOCUMENTS

| BR | 9 402 197 A | | 1/1996 |
|---|---|---|---|
| EP | 0 343 330 A2 | | 11/1989 |
| EP | 1 992 322 A1 | | 11/2008 |
| FR | 2 674 126 A1 | | 9/1992 |
| FR | 2 815 852 A1 | | 5/2002 |
| HU | 9 700 451 A2 | | 5/1998 |
| JP | 03 161412 A | | 7/1991 |
| JP | 06 040882 A | | 2/1994 |
| JP | 2002 212050 A | | 7/2002 |
| JP | 2002 226323 A | | 8/2002 |
| JP | 2003 342119 A | | 12/2003 |
| JP | 2005 281205 A | | 10/2005 |
| JP | 2006 008571 A | | 1/2006 |
| JP | 2007 143452 A | | 6/2007 |
| JP | 2007143452 A | * | 6/2007 |
| JP | 2008031049 A | * | 2/2008 |
| JP | 2008 184439 A | | 8/2008 |
| JP | 2008 184440 A | | 8/2008 |
| WO | 2007/119227 A2 | | 10/2007 |

OTHER PUBLICATIONS

Codogno et al.: "Autophagy and signaling: their role in cell survival and cell death", Cell Death and Differentiation, vol. 12, 2005, pp. 1509-1518, XP002541242, p. 1509, col. 2, last paragraph, p. 1510, col. 2, paragraph 2, p. 1511, col. 2, paragraph 3, p. 1512, figure 1.
Donati: "The involvement of macroautophagy in aging and anti-aging interventions", Molecular Aspects of Medicine, vol. 27, 2006, pp. 455-470, XP005681057, p. 462-p. 465.
International Search Report, dated Apr. 26, 2010, from corresponding PCT application.

* cited by examiner

*Primary Examiner* — Qiuwen Mi
(74) *Attorney, Agent, or Firm* — Young & Thompson

(57) ABSTRACT

The object of the invention is the use in a cosmetic composition of an effective amount of at least one cutaneous cell autophagy activator as a cosmetic active ingredient. The invention also relates to cosmetic compositions that include at least one cutaneous cell autophagy activator as a cosmetic active ingredient 5 and a cosmetic process for detoxifying skin and/or for preventing or combating cutaneous aging.

11 Claims, No Drawings

COSMETIC USE OF SKIN CELL AUTOPHAGY ACTIVATORS

This application is a division of application Ser. No. 13/133,046 filed on Jun. 6, 2011; which is the 35 U.S.C. 371 national stage of International application PCT/FR2009/052410 filed on Dec. 4, 2009; which claims priority to French application 0858308 filed on Dec. 5, 2008. The entire contents of each of the above-identified applications are hereby incorporated by reference.

This invention relates to the use—in a cosmetic composition—of an activator of the autophagy of cells of the skin as a cosmetic active ingredient.

The object of the invention is also cosmetic compositions that comprise at least one activator of the autophagy of cells of the skin as a cosmetic active ingredient as well as a cosmetic process for detoxifying the skin and/or for preventing or combating cutaneous aging, comprising the topical application of such compositions on the skin.

The skin, organ in contact with the environment, is constantly subjected to damage, both from the outside and from the inside, which threatens its balance and alters its appearance.

It is known, for example, that excessive exposure to ultraviolet rays (UV) is reflected by various cutaneous manifestations, such as actinic erythemas, solar elastosis, or else the premature appearance of the effects of cutaneous aging: the skin becomes loose, deeply wrinkled, rough, dry, sprinkled with hypopigmented or hyperpigmented spots and dilated vessels. These manifestations, which reflect profound structural changes in the cutaneous tissue, are unsightly and ugly, and many people have a tendency to want to smooth them out.

This is why the objective of this invention is to propose an effective means for protecting the skin against damage that can alter its proper operation and its appearance and for combating the manifestations that follow therefrom.

To respond to this, this invention proposes using at least one activator of the autophagy of cells of the skin, in particular keratinocytes and fibroblasts, as a cosmetic active ingredient in a cosmetic composition.

Actually, the use of at least one cutaneous cell autophagy activator makes it possible to combat the accumulation of deleterious molecules in the cutaneous cells that are produced in the case of stress and thus to combat the manifestations that follow therefrom.

In particular, the purpose of the invention is the use in a cosmetic composition of at least one activator of the autophagy of cells of the skin, in particular keratinocytes and/or fibroblasts, as an active ingredient, for detoxifying the cutaneous cells, combating the aging of the skin, restructuring the skin, hydrating and protecting the horny layer, increasing cellular renewal, protecting the cells from the harmful effects of UVA and UVB radiation, and limiting the inflammation phenomena.

Preferably, the purpose of the invention is the use in a cosmetic composition of at least one activator of the autophagy of cells of the skin, as an active ingredient that is designed to detoxify the cells of the skin and/or to combat the cutaneous aging.

Advantageously, by increasing the autophagy mechanism in the cutaneous cells, the use according to the invention makes it possible to increase the elimination of damaged molecules, to detoxify the skin, and to limit the cutaneous aging.

Actually, under certain conditions, in particular with age and overexposure to sun, the cells of the skin are no longer in a state to evacuate the molecules that are damaged by the radiation and the various stresses. The cells are engorged with these damaged molecules and with free radicals. The cosmetic use of cutaneous cell autophagy activators according to the invention makes it possible to limit this cellular engorgement and to remove therefrom the cells of deleterious and useless elements that impede its optimal operation by accumulating.

The object of the invention is also a cosmetic composition for topical application on the skin that comprises—in a physiologically acceptable medium—an effective amount of at least one cutaneous cell autophagy activator that is selected from among active ingredients that originate from *Lithothamnium calcareum, Melilotus officinalis, Citrus limonum, Candida saitoana, Lens culinaris, Averrhoa carambola, Momordica charantia, Yarrowia lipolytica* and at least one cosmetic adjuvant. Preferably, the cutaneous cell autophagy activator is present in an amount that is between 0.1 and 15% by weight relative to the total weight of the composition.

Finally, the invention also has as its object a cosmetic process for detoxifying the skin and/or for preventing or combating cutaneous aging, comprising the topical application on the skin of a composition that comprises at least one activator of the autophagy of cells of the skin.

The invention is now described in detail.

The purpose of this invention is therefore the use in a cosmetic composition of an autophagy activator as a cosmetic active ingredient.

Autophagy is a mechanism for recycling and detoxifying cellular components and organites. In particular, autophagy makes it possible to regulate, repair and eliminate proteins with a long service life in the cells, thus ensuring a control during differentiation and aging of human skin.

On the cellular plane, the autophagy mechanism comprises four stages: initiation, formation of an initial vacuole, named autophagosome, which sequesters the cytoplasmic material, the maturation of the autophagosome into a degradative vacuole, and fusion with the lysosome until the degradation of the sequestered material is achieved.

According to a first aspect, a cutaneous cell autophagy activator that is useful according to the invention can be an active ingredient that has a stimulating activity of the expression of MAP-LC3 ("microtubule-associated membrane protein," membrane proteins combined with microtubules) and/or ATG5-12 ("autophagy-related genes," genes of autophagy) of cells of the skin.

Actually, the formation of the autophagosome, an essential stage in the mechanism of the autophagy, involves two coupling systems: the complex ATG5-12 and the MAP-LC3.

The first stage of the autophagy is the formation of a multi-membrane structure, called a phagophore, whose origin remains unknown. This structure is extended to form the autophagosome that sequesters the cytoplasmic material. The autophagosome fuses with the lysosome, and its content is then degraded by the lysosomal enzymes. During the formation of the autophagosome, ATG proteins are engaged starting from cytoplasm and are combined temporarily with the autophagosomal membrane.

This process primarily involves three protein complexes: the PI(3)K of Class III combined with the protein Beclin-1 and two coupling systems. The early event in the induction of the formation of the autophagosome is the production of phosphatidyl inositol 3-phosphate by the complex Beclin-1-PI(3)K of Class III that makes possible the engagement of the first coupling system ATG12-ATG5, also referred to as ATG5-12. The latter, in turn, makes possible the coupling of the phosphatidyl ethanolamine (PE) with the protein MAP- LC3 for forming the conjugate MAP-LC3-PE, which is then engaged with the autophagosomal membrane.

The ATG genes are therefore involved in the formation of the autophagosome, and ATG5-12 is a precursor of the coupling of MAP-LC3 and phosphatidyl ethanolamine (PE).

The MAP-LC3 are proteins of 15 kDa that are present in mammals They are used at the time of the formation of membranes of the autophagosomes. There are two forms of them: a cystolic form, the LC3-I, and a form that is linked to the membrane LC3-II.

In a first step, the MAP-LC3 are cleaved directly after their synthesis, at their C-terminal part so as to provide the LC3-I cystolic form. During the autophagy, LC3-I is converted into LC3-II, and the proteins are combined with autophagic vacuoles.

Thus, the use of an active ingredient that has a stimulating activity of the expression of MAP-LC3 and/or ATG5-12 of the cells of the skin makes it possible to stimulate the formation of the autophagosome and therefore to stimulate the autophagy of cells of the skin.

According to a second aspect, an activator of the autophagy of cutaneous cells that is useful according to the invention can be an active ingredient that inhibits the activation of phosphorylated mTOR.

The complex mTOR ("mammalian Target Of Rapamycin" or target of the rapamycin of mammals) is a molecule that is involved in the initiation of the formation of the autophagosome. It plays a role of sensor of the ATP and amino acids regulating the balance between the availability of nutrients and cellular growth.

When the amount of nutrients is sufficient, mTOR is phosphorylated on serine 2448 and transmits a positive signal that activates the cellular growth and inhibits autophagy.

If this is not the case, i.e., under conditions of nutritional deprivation or starvation, this phosphorylation disappears in favor of a phosphorylation of threonine 2446, which makes it possible to lift the inhibition of autophagy.

The autophagy mechanism is therefore initiated when there is dephosphorylation of mTOR on serine 2448.

Thus, the cosmetic use of an active ingredient that inhibits the activity of mTOR in the cells of the skin makes it possible to promote the initiation of autophagy, to mobilize the formation of autophagosomes, and therefore to stimulate the autophagy of cells of the skin.

According to a final aspect, a stimulator of the autophagy activity of the cutaneous cells that is useful according to the invention can be an active ingredient that has a stimulating activity of the expression of the protein p53, the AMPK, and/or DRAM.

The protein p53 is a major protein of stress, capable of, in particular:
  Activating the protein DRAM ("Damage Regulated Autophagy Modulator," modulator of damage regulated by autophagy), a protein that is directly involved in the initiation of the autophagy mechanism, and
  Inhibiting mTOR by means of the activation of a protein kinase, AMPK.

The activation of DRAM and/or AMPK, either directly or by means of p53, therefore makes it possible to stimulate autophagy.

Thus, the cosmetic use of an active ingredient that has a stimulating activity of the expression of the phosphorylated protein p53, DRAM and/or AMPK of the cells of the skin makes it possible to promote the initiation of autophagy, to mobilize the formation of the autophagosomes, and therefore to stimulate the autophagy of cells of the skin.

The cellular consequence of an activation of the autophagy mechanism by an active ingredient that has a stimulating activity of the expression of MAP-LC3, ATG5-12, the phosphorylated protein p53, DRAM and/or AMPK and/or that has an inhibiting activity of phosphorylated mTOR is a better detoxification of the cells, i.e., a reduction of the reactive oxidized radicals and degenerated macromolecules that are locked in the cutaneous cells. Preferably, the stimulator of the cutaneous cell autophagic activity that is useful according to the invention is an active ingredient that originates from at least one plant, one algae or one yeast.

In a preferred way, the autophagy activator is an active ingredient that originates from at least one algae of the *Lithothamnium calcareum* type, or a plant that is selected from among *Melilotus officinalis, Citrus limonum, Lens culinaris, Averrhoa carambola, Momordica charantia*, or a yeast that is selected from among *Candida saitoana* and *Yarrowia lipolytica*.

According to one aspect of the invention, the cutaneous cell autophagy activator can be selected by a test that is executed on cultures of cutaneous cells that comprise the following stages:
  Cultivation of cutaneous cells, keratinocytes or fibroblasts, within a suitable culture medium,
  Removal of the culture medium and replacement by a culture medium that comprises a stressing agent that induces a nutritive and/or oxidative stress,
  Addition of an active ingredient that originates from a plant, algae or yeast that is to be tested within the culture medium,
  Removal of the oxidizing agent and replacement of the culture medium by a culture medium that comprises the active ingredient, and
  Analysis of the expression of MAP-LC3, ATG5-12, phosphorylated mTOR, phosphorylated protein p53, the expression of the protein DRAM and/or AMPK by said cells, and comparison of the results with those that are obtained on cultures of cutaneous cells that are not treated with the extract to be tested.

If an increase of the expression of MAP-LC3, ATG5-12, the phosphorylated protein p53, the protein DRAM and/or AMPK, and/or a reduction of phosphorylated mTOR is noted, then the tested active ingredient can be used in a cosmetic composition as an activator of the autophagy of cells of the skin.

To illustrate the invention, several active ingredients have been tested for studying their capacity to increase the autophagy of cutaneous cells.

First, it was verified that the induction of stress at the cells of the skin duly produced an increase of the autophagy.

Next, the level of autophagy of young and old cells, subjected to the same oxidative and nutritive stresses, was compared.

Finally, active ingredients were selected by the execution of the test process according to the invention.

1/Visualization of the Cutaneous Cell Autophagy After Nutritive Stress

The protocol that is executed consists in subjecting HaCaT-type keratinocyte cultures or normal human keratinocytes to nutritive stress, i.e., to an absence of growth factors, for a certain period, and to evaluate the expression of several autophagy markers during the cellular recovery.

The protocol is as follows:
  Cultures of cells of the skin for 24 hours in the complete culture medium (with growth factors),
  Removal of the complete culture medium and replacement by a non-nutritive culture medium (without a growth factor). The cells are cultivated for some time (from 0.5 hour to 24 hours) in a state of nutritive stress, After these cultivation times in a state of nutritive stress, removal of the non-nutritive culture medium and replacement by the complete culture medium, and finally Evaluation of the autophagy state of cutaneous cells by evaluation of the expression of MAP-LC3, the complex ATG5-12, phosphorylated mTOR, phosphorylated p53, DRAM and phosphorylated AMPK after cellular recovery.

1.1/Evaluation of the Expression of MAP-LC3 After Nutritive Stress

It is possible to evaluate the autophagy of cutaneous cells by visualizing the expression of the protein MAP-LC3 by immunofluorescent marking.

The expression of MAP-LC3 was evaluated on cultures of cutaneous cells of lines HaCaT and on normal human keratinocytes after different contact times of the nutritive stress. With the immunomarking results being qualitative, several levels of expression of MAP-LC3 were defined:

| Very low detection of immunoreactivity | − |
| Low detection of immunoreactivity | ± |
| Medium detection of immunoreactivity | + |
| Strong detection of immunoreactivity | ++ |

The results that are obtained are presented in the table below:

| Cultivation Times in a State of Nutritive Stress (Hours) | Expression of MAP-LC3 |
|---|---|
| 0 | − |
| 0.5 | − |
| 1 | − |
| 2 | + |
| 3 | + |
| 4 | ++ |
| 8 | + |
| 24 | − |

During the cultivation of the HaCaT keratinocytes in the state of nutritive stress, the clear appearance of a point marking MAP-LC3 at the cytoplasm of cells is observed. This marking reflects the formation of autophagosomes in the keratinocytes subjected to nutritive stress.

This marking can be observed upon two hours of starvation and reaches a maximum after four hours of starvation.

These nutritive stress conditions therefore make it possible to induce the formation of autophagosomes and consequently an autophagy, visualized by the expression of MAP-LC3.

1.2/Evaluation of the Expression of the Complex ATG5-12 After Nutritive Stress

It is also possible to evaluate the autophagy of cutaneous cells by visualizing the expression of the complex ATG5-12 by immunofluorescent marking.

The evaluation of the expression of the complex ATG5-12 was executed on cultures of cutaneous cells of lines HaCaT and on normal human keratinocytes after different times of cultivation in a state of nutritive stress. With the immunomarking results being qualitative, several levels of expression of ATG5-12 were defined:

| Very low detection of immunoreactivity | − |
| Low detection of immunoreactivity | ± |
| Medium detection of immunoreactivity | + |
| Strong detection of immunoreactivity | ++ |
| Very strong detection of immunoreactivity | +++ |

The results that are obtained are presented in the table below:

| Cultivation Times in a State of Nutritive Stress (Hours) | Expression of ATG5-12 |
|---|---|
| 0 | ± |
| 1 | ++ |
| 2 | ++ |
| 3 | ++ |
| 4 | + |

During the cultivation of the HaCaT keratinocytes in a state of nutritive stress, the clear appearance of a point marking ATG5-12 at the cytoplasm of cells is observed. This marking reflects the formation of autophagosomes in the keratinocytes that are subjected to nutritive stress.

This marking can be observed upon one hour and up to three hours of starvation.

The nutritive stress conditions therefore make it possible to induce an autophagic-type phenomenon, visualized by the expression ATG5-12.

1.3/Evaluation of the Expression of Phosphorylated mTOR after Nutritive Stress

It is also possible to evaluate the autophagy of cutaneous cells by visualizing the expression of mTOR that is phosphorylated by Western Blott.

The evaluation of the expression of phosphorylated mTOR has been evaluated on cultures of cutaneous cells of lines HaCaT and on normal human keratinocytes after different cultivation times in a state of nutritive stress. The expression of phosphorylated mTOR is presented in the table below in percentage relative to the control (without nutritive stress).

| Cultivation Times in a State of Nutritive Stress (Hours) | Expression of Phosphorylated mTOR (%) |
|---|---|
| 0 | 100 |
| 2 | 118 |
| 4 | 122 |
| 8 | 78 |
| 12 | 64 |
| 24 | 58 |

This experiment showed a significant reduction of the phosphorylated protein mTOR that is visible upon eight hours of deprivation in the cultures of cutaneous cells subjected to starvation.

When the phosphorylated protein mTOR decreases, the inhibition of the autophagy is lifted.

The nutritive stress conditions therefore make it possible to induce autophagy on cultures of cutaneous cells, visualized by the reduction of the phosphorylated mTOR expression.

1.4/Evaluation of the Expression of Phosphorylated p53 after Nutritive Stress

It is also possible to evaluate the autophagy of cutaneous cells by visualizing the expression of the phosphorylated protein p53 by Western Blott.

The evaluation of the expression of the phosphorylated protein p53 was evaluated on cultures of cutaneous cells of lines HaCaT and on normal human keratinocytes after different cultivation times in a state of nutritive stress. The expression of phosphorylated p53 is presented in the table below in percentage relative to the control (without nutritive stress).

| Cultivation Times in a State of Nutritive Stress (Hours) | Expression of Phosphorylated p53 (%) |
|---|---|
| 0 | 100 |
| 0.5 | 140 |
| 1 | 170 |
| 1.5 | 168 |
| 2 | 161 |

This experiment showed a significant increase of the expression of the phosphorylated protein p53 that is visible upon one hour in cell cultures subjected to starvation.

The nutritive stress conditions therefore make it possible to induce an autophagic-type phenomenon on cultures of cutaneous cells, visualized by the increase of the expression of the phosphorylated protein p53.

1.5/Evaluation of the Expression of the Protein DRAM After Nutritive Stress

It is also possible to evaluate the autophagy of cutaneous cells by visualizing the expression of the protein DRAM, by Western Blott, on cultures of cutaneous cells of lines HaCaT and on normal human keratinocytes after different cultivation times in a state of nutritive stress. The expression of DRAM is presented in the table below in percentage relative to the control (without nutritive stress).

| Cultivation Times in a State of Nutritive Stress (Hours) | Expression of the Protein DRAM (%) |
|---|---|
| 0 | 100 |
| 0.5 | 260 |
| 1 | 220 |
| 1.5 | 330 |
| 2 | 95 |

This experiment showed a significant increase of the expression of the protein DRAM after 0.5 hour of cultivation in a state of nutritive stress. The expression of the protein DRAM peaks after 1.5 hours of cultivation in a state of nutritive stress. This coincides with the kinetics of expression of the protein p53 that reaches its maximum after one hour of nutritive stress.

The nutritive stress conditions therefore make it possible to induce an autophagic-type phenomenon on cultures of cutaneous cells, visualized by the increase of the expression of the protein DRAM.

1.6/Evaluation of the Expression of the Phosphorylated Protein AMPK After Nutritive Stress It is also possible to evaluate the autophagy of cutaneous cells by visualizing the expression of the phosphorylated protein AMPK, by Western Blott, on cultures of cutaneous cells of lines HaCaT and on normal human keratinocytes after different cultivation times in a state of nutritive stress. The expression of DRAM is presented in the table below in a percentage relative to the control (without nutritive stress).

| Cultivation Times in a State of Nutritive Stress (Hours) | Expression of Phosphorylated AMPK (%) |
|---|---|
| 0 | 98 |
| 0.5 | 155 |
| 1 | 170 |
| 1.5 | 172 |
| 2 | 130 |

This experiment showed that the expression of phosphorylated AMPK is increased upon 0.5 hour of cultivation in a state of nutritive stress and peaks at 1.5 hours. This coincides with the kinetics of expression of the protein p53 that reaches its maximum after one hour of nutritive stress.

The nutritive stress conditions therefore make it possible to induce an autophagic-type phenomenon on cultures of cutaneous cells, visualized by the increase of the expression of the phosphorylated protein AMPK.

These studies have therefore made it possible to show that the autophagy mechanism can be equally visualized on stressed cutaneous cell cultures by the evaluation of the expression of different proteins such as MAP-LC3, the complex ATG5-12, phosphorylated mTOR, the phosphorylated protein p53, the protein DRAM or the phosphorylated protein AMPK.

2/Visualization of the Autophagy of Cutaneous Cells After a Nutritive and Oxidative Stress The visualization of the autophagy is possible, as in the case of the nutritive stress, by the evaluation of different proteins such as MAP-LC3, the complex ATG5-12, the phosphorylated protein mTOR, the phosphorylated protein p53, the protein DRAM or the phosphorylated protein AMPK. In this experiment, the expression of the autophagy of cutaneous cells was studied by analyzing the expression of MAP-LC3, the phosphorylated protein p53, and the protein DRAM in the stressed cutaneous cell cultures.

The protocol is as follows:

Cultivation of cells for 24 hours in a complete culture medium.

Removal of the culture medium and replacement with the non-nutritive culture medium that contains the oxidizing agent $H_2O_2$ for 3 hours (different doses of $H_2O_2$—125 µM and/or 250 µM—have been tested).

Removal of the oxidizing agent and the non-nutritive culture medium, replacement by a complete culture medium without an oxidizing agent.

Evaluation of the expression of MAP-LC3, the phosphorylated protein p53, or the protein DRAM after cellular recovery. Several recovery times have been selected (0.5 hour, 1 hour, 1.5 hours, or 2 hours of recovery).

2.1/Evaluation of the Expression MAP-LC3 After Nutritive and Oxidative Stress

It is possible to evaluate the autophagy of stressed cutaneous cells by visualizing the expression of the protein MAP-LC3 by immunofluorescent marking.

The evaluation of the expression MAP-LC3 was analyzed under these moderate stress conditions (125 µM and 250 µM of hydrogen peroxide $H_2O_2$) on HaCaT keratinocyte cultures and on normal human keratinocytes. With the immunomarking results being qualitative, several levels of expression of ATG5-12 were defined:

| | |
|---|---|
| Very low detection of immunoreactivity | − |
| Low detection of immunoreactivity | ± |
| Medium detection of immunoreactivity | + |

-continued

| | |
|---|---|
| Strong detection of immunoreactivity | ++ |
| Very strong detection of immunoreactivity | +++ |

The results that are obtained are presented in the table below:

| | Recovery Time (Hours) | Expression of MAP-LC3 |
|---|---|---|
| Without Stress | 2 | + |
| $H_2O_2$, 125 µM | 0.5 | ++ |
| | 1 | ++ |
| | 1.5 | +++ |
| | 2 | ++ |
| $H_2O_2$, 250 µM | 0.5 | ++ |
| | 1 | +++ |
| | 1.5 | ++ |
| | 2 | + |

For the 125 µM dose of oxidative stress, the point marking of MAP-LC3 at the cytoplasm of cells is observed upon 0.5 hour of recovery, which peaks after 1.5 hours, and then is minimized from two hours of recovery.

For the 250 µM dose, it is noted that this marking appears upon 0.5 hour, reaches a maximum at 1 hour, and is reduced upon 1.5 hours of recovery.

The nutritive and oxidative stress conditions therefore make it possible to induce an autophagic-type phenomenon, visualized by the increase of the expression of MAP-LC3 in the cutaneous cells.

2.3/Evaluation of the Expression of the Phosphorylated Protein p53 After Nutritive and Oxidative Stress It is also possible to evaluate the autophagy of stressed cutaneous cells by visualizing the expression of the phosphorylated protein p53 by Western Blott.

The evaluation of the expression of the phosphorylated protein p53 has therefore been analyzed under these moderate stress conditions with 125 µM of $H_2O_2$ on HaCaT keratinocyte cultures and on normal human keratinocytes. The expression of phosphorylated p53 is presented in the table below in percentage relative to the control (without stress).

| | Recovery Time (Hours) | Phosphorylated Expression p53 (%) |
|---|---|---|
| Without Stress | 2 | 100 |
| $H_2O_2$, 125 µM | 0.5 | 221 |
| | 1 | 140 |
| | 2 | 128 |

For the 125 µM dose of nutritive and oxidative stress, it is observed that the marking of the phosphorylated protein p53 is at its maximum after 0.5 hour of recovery, and then it is gradually minimized.

The oxidative stress conditions therefore make it possible to induce an autophagic-type phenomenon, visualized by the increase of the expression of the phosphorylated protein p53.

2.4/Evaluation of the Expression of the Protein DRAM After Nutritive and Oxidative Stress It is also possible to evaluate the autophagy of stressed cutaneous cells by visualizing the expression of the protein DRAM by Western Blott.

The evaluation of the expression of DRAM was therefore analyzed under these moderate stress conditions with 125 µM of $H_2O_2$ on HaCaT keratinocyte cultures and on normal human keratinocytes. The expression of DRAM is presented in the table below in percentage relative to the control (without stress).

| | Recovery Time (Hours) | Expression of DRAM (%) |
|---|---|---|
| Without Stress | 2 | 100 |
| $H_2O_2$, 125 µM | 0.5 | 120 |
| | 1 | 180 |
| | 1.5 | 390 |
| | 2 | 200 |

It is noted that a nutritive and oxidative stress on the cutaneous cell cultures increase the expression of the protein DRAM.

For the 125 µM dose of oxidative stress, it is observed that the marking of the protein DRAM is at its maximum after 1.5 hours of recovery, and then it is minimized starting from 2 hours.

The conditions of nutritive and oxidative stress therefore make it possible to induce an autophagic-type phenomenon.

These studies have therefore made it possible to show that the autophagy mechanism can be visualized on cutaneous cell cultures that are stressed by the evaluation of the expression of different proteins such as MAP-LC3, the phosphorylated protein p53, or the protein DRAM.

3/Comparison of the Autophagy in Young or Aged Cells

This study has as its objective to compare the autophagy level of young cells (from donors with a mean age of 26 years) and aged cells (from donors with a mean age of 70 years) that are subjected to the same oxidative and nutritive stresses.

The evaluation of the autophagy level was considered by the analysis of the expression of the protein MAP-LC3 by Western Blott.

The protocol that is put into place is as follows:
Cultures of so-called young or aged cells for 24 hours in the complete culture medium,
Removal of the complete culture medium, replacement with the non-nutritive culture medium that contains the oxidizing agent $H_2O_2$ for 3 hours at different doses,
Removal of the oxidizing agent, replacement by the complete culture medium without an oxidizing agent,
Evaluation of the expression of MAP-LC3 after cellular recovery.

The results are described in the table below in percentage relative to the control (without stress).

| | Expression of MAP-LC3 | |
|---|---|---|
| | On Young Cells | On Aged Cells |
| Without Stress | 100 | 100 |
| $H_2O_2$, 125 µM | 172 | 138 |
| $H_2O_2$, 250 µM | 322 | 187 |
| $H_2O_2$, 400 µM | 168 | 135 |
| $H_2O_2$, 600 µM | 143 | 96 |
| $H_2O_2$, 1000 µM | 117 | 92 |

Under the conditions of this study, the so-called young cutaneous cells show an increase of the expression of MAP-LC3 when they are subjected to a moderate oxidative stress (125, 250, see 400 µM). When they are subjected to a significant oxidative stress (600 and 1,000 µM), they are placed in apoptosis.

The so-called aged cutaneous cells do not have the same increase of the expression MAP-LC3 when they are subjected to the same moderate oxidative stress.

This difference in the way that aged cells were put into autophagy compared to the young cells is significant.

This study therefore shows that aged cells are no longer capable of being protected and of detoxifying during a moderate nutritive and oxidative stress.

4/Screening of Active Ingredients Increasing the Autophagy of Cutaneous Cells

The screening is executed according to the protocol of nutritive and oxidative stress presented in Item 2.1, starting from active ingredients originating from plants, algae or yeasts. The evaluation of the effect of active ingredients on the autophagy of cutaneous cells has been carried out by analyzing the expression of the protein MAP-LC3 in cutaneous cell cultures subjected to a nutritive and oxidative stress.

The protocol of the test is as follows:
Cultivations of cells for 24 hours in a complete culture medium,
Removal of the complete culture medium, replacement with the non-nutritive culture medium that contains the oxidizing agent H2O2 for 3 hours that may or may not be in the presence of active ingredients,
Removal of the oxidizing agent and the non-nutritive culture medium, replacement by the complete culture medium that may or may not be in the presence of the active ingredients,
Evaluation of the expression of MAP-LC3 after cellular recovery by immunofluorescent marking.

The tested active ingredients have been produced according to the following protocol:
Solubilization of plant, algae or yeast powder in water at a rate of 50 g/l (m/v),
Enzymatic hydrolysis,
Separation of soluble and insoluble phases,
Filtration and sterilizing filtration.

The primary active ingredients are:

| Active Ingredient | Plants or Yeasts that are Used |
|---|---|
| Active ingredient originating from Lithothamnium | Lithothamnium calcareum |
| Active ingredient originating from Melilot | Melilotus officinalis |
| Active ingredient originating from lemon | Citrus limonum |
| Active ingredient originating from Candida saitoana | Candida saitoana |
| Active ingredient originating from lentils | Lens culinaris |
| Active ingredient originating from stinging nettles | Urtica dioica |
| Active ingredient originating from carambola | Averrhoa carambola |
| Active ingredient originating from momordica | Momordica charantia |
| Active ingredient originating from Yarrowia lipolytica | Yarrowia lipolytica |

The results of the most effective active ingredients that are selected and tested in triplicate are described in the following table:

| | Expression of MAP-LC3 |
|---|---|
| Without active ingredient | ± |
| Active ingredient originating from Lithothamnium | +++ |
| Active ingredient originating from Melilot | ++ |
| Active ingredient originating from lemon | ++ |
| Active ingredient originating from Candida saitoana | ++ |
| Active ingredient originating from lentils | + |
| Active ingredient originating from stinging nettles | + |
| Active ingredient originating from carambola | + |
| Active ingredient originating from momordica | + |
| Active ingredient originating from Yarrowia lipolytica | + |

These active ingredients therefore make it possible to increase the autophagy of cutaneous cells that are subjected to a moderate nutritive and oxidative stress and thus to detoxify the skin and to prevent or combat the cutaneous aging.

These active ingredients can be incorporated in cosmetic compositions.

5. Examples of Cosmetic Compositions that Contain an Active Ingredient that Acts on the Autophagy of Cutaneous Cells The invention also covers the cosmetic compositions, including at least one active ingredient that acts on the autophagy of cutaneous cells in different galenical forms, suitable for administration by cutaneous topical means.

These compositions can come in particular in the form of creams, oil-in-water emulsions, water-in-oil emulsions, multiple emulsions, solutions, suspensions or powders. They can be more or less fluid and have the appearance of a cream, a lotion, a milk, a serum, an ointment, a gel, a paste or a foam, or in solid form.

These compositions contain between 0.01 and 15% by weight of active ingredient(s) acting on the autophagy of cutaneous cells according to this invention, preferably between 1% and 4%.

5.1. Expert Cream

An example of a cream that comprises an active ingredient that is extracted from lemon, as presented in Item 4, can have the following composition:

| | | |
|---|---|---|
| A. | Water | Enough to produce 100% |
| | Glycerol (Univar) | 3.33% |
| | EDTA | 0.13% |
| | Satialgine (Degussa) | 0.66% |
| | Talc (Luzenac) | 1% |
| B. | Miglyol 812 (Condea Chemie) | 3.33% |
| | Ritaphyl ICS (Rita) | 1.33% |
| | Ritachol SS (Rita) | 1.33% |
| | Ipm (Univar) | 3.33% |
| | Ritalan C (Rita) | 1.33% |
| | Montanov 14 (Seppic) | 1.33% |
| | Lanol 14M (Seppic) | 1.33% |
| | Brij 72 (Uniquema) | 1% |
| | Brij 721 (Uniquema) | 0.33% |
| C. | Phenoxyethanol (Sigma) | 0.9% |
| | Ethylhexylglycerin (Seppic) | 0.1% |
| D. | Active ingredient originating from lemon according to the invention | 4% |

The cream is obtained by the execution of the following stages:
Heating A and B to 80° C., while being stirred mechanically,
Emulsifying B in A while being stirred,
At 30° C., adding C in order, and
Continuing the homogenization until the cream is uniform.

5.2 Anti-Wrinkle Cream

An example of a cream that comprises an active ingredient that is extracted from lithothamnium, as presented in Item 4, can have the following composition:

| | | |
|---|---|---|
| A. | Water | Enough to produce 100% |
| | Butylene glycol (Univar) | 3% |
| B. | Isohexadecane (Laserson) | 5% |
| | Rita IPP (Rita) | 2% |
| | Montanov 202 (Seppic) | 3% |
| | Arlacel 161 (Uniquema) | 1% |
| | Ritox 59 (Rita) | 1% |
| | Lanette O (Cognis) | 1% |
| C. | Phenoxyethanol (Sigma) | 0.9% |
| | Ethylhexylglycerin (Seppic) | 0.1% |
| | DC 200 (Dow Corning) | 0.5% |
| | Active ingredient originating from Lithothamnium according to the invention | 4% |
| D. | Sepigel 305 (Seppic) | 4% |

The cream is obtained by the execution of the following stages:

Mixing A, mixing B, and heating A and B to 80° C., while being stirred mechanically,
Emulsifying B in A while being stirred,
At 30° C., adding C in order, and
Continuing the homogenization until the cream is uniform.

5.3 Night Cream

An example of a cream that comprises an active ingredient that is extracted from Melilothus, as presented in Item 4, can have the following composition:

| | | |
|---|---|---|
| A. | Water | Enough to produce 100% |
| | Carbopol ETD 2020 (Noveon) | 0.4% |
| B. | Cetyl alcohol (Stearinerie Dubois) | 3% |
| | Stearyl alcohol (Stearinerie Dubois) | 3% |
| | DUB MCT 5545 (Stearinerie Dubois) | 4.5% |
| | DC 345 (Dow Corning) | 7.5% |
| | Monomuls 900 18 (Henkel) | 3% |
| C. | Phenoxyethanol (Sigma) | 0.9% |
| | Ethylhexylglycerin (Seppic) | 0.1% |
| | Active ingredient that originates from Melilotus according to the invention | 4% |
| D. | NaOH | Enough to produce pH 4.5 |

The cream is obtained by the execution of the following stages:

Mixing A, thoroughly dispersing the gel and mixing B,
Heating A and B to 80° C.,
Emulsifying B in A while being stirred,
At 40° C., adding C in order,
Continuing the homogenization until the cream is uniform,
Adjusting the pH with D, and
Allowing it to cool to 30° C. while being stirred.

5.4 Cream for Mature Skin

An example of cream that comprises an active ingredient that is extracted from Candida saitoana, as presented in Item 4, can have the following composition:

| | | |
|---|---|---|
| A. | Water | Enough to produce 100% |
| | Glycerol (Univar) | 1.75% |
| | Propylene glycol (Univar) | 6.5% |
| | Aculyne 33A (ISP) | 2.5% |
| | Carbopol EDT 2020 (Goodrich) | 0.5% |
| B. | Cetiol SN (Cognis) | 3% |
| | Eumulgine B1 (Cognis) | 1.75% |
| | Ritaphyl ICS (Rita) | 3% |
| | Patlac IL (Rita) | 3% |
| | Isopropyl myristat (Univar) | 3% |
| | Montane 80 (Seppic) | 1.5% |
| | Montanox 60 (Seppic) | 1.5% |
| | DC 345 (Dow Corning) | 3% |
| C. | Phenoxyethanol (Sigma) | 0.9% |
| | Ethylhexylglycerin (Seppic) | 0.1% |
| D. | Active ingredient that originates from Candida saitoana | 4% |
| | NaOH | Enough to produce pH 5.5 |

The cream is obtained by the execution of the following stages:

Mixing A, mixing B, and heating A and B to 80° C.,
Emulsifying B in A while being stirred,
At 30° C., adding C and D,
Adjusting to pH 5.5 with NaOH, and
Continuing homogenization until the cream is uniform.

I claim:

1. A cosmetic process for detoxifying the skin and/or for combating cutaneous aging, comprising the topical application on the skin of a composition that comprises at least one activator of the autophagy of cells of the skin,
said cutaneous cell autophagy activator being selected based on the results of a test executed in vitro on a culture of cutaneous cells, the test comprising:
cultivating cutaneous cells, keratinocytes or fibroblasts with a suitable culture medium;
removing the culture medium and replacing the medium with a culture medium comprising a stress agent that induces a nutritive and/or oxidative stress;
providing an active ingredient to be tested, said ingredient originating from a plant, algae or yeast;
removing the culture medium comprising the stress agent and replacing the medium with a culture medium comprising the active ingredient;
analyzing the expression of at least one of MAP-LC3, ATG5-12, phosphorylated mTOR, phosphorylated protein p53, DRAM and AMPK by the cultured cutaneous cells;
comparing the results of said analysis with results obtained on a control culture of the cutaneous cells that are not treated with the active ingredient; and
selecting an active ingredient that has at least one of the following activities:
a stimulating activity on expression of MAP-LC3,
a stimulating activity on expression of ATG5-12,
a stimulating activity on expression of phosphorylated protein p53,
a stimulating activity on expression of DRAM,
a stimulating activity on expression of AMPK, and
an inhibiting activity on expression of phosphorylated mTOR.

2. The cosmetic method according to claim 1, wherein said cutaneous cell autophagy activator is an active ingredient that has a stimulating activity on expression of MAP-LC3.

3. The cosmetic method according to claim 1, wherein said cutaneous cell autophagy activator is an active ingredient that has a stimulating activity on expression of ATG5-12.

4. The cosmetic method according to claim 1, wherein said cutaneous cell autophagy activator is an active ingredient that has a stimulating activity on expression of phosphorylated protein p53.

5. The cosmetic method according to claim 1, wherein said cutaneous cell autophagy activator is an active ingredient that has a stimulating activity on expression of DRAM.

6. The cosmetic method according to claim 1, wherein said cutaneous cell autophagy activator is an active ingredient that has a stimulating activity on expression of AMPK.

7. The cosmetic method according to claim 1, wherein said cutaneous cell autophagy activator is an active ingredient that inhibits activation of phosphorylated mTOR.

8. The cosmetic method according to claim 1, wherein said cutaneous cell autophagy activator is an active ingredient that originates from at least one algae of type *Lithothamnium calcareum*, or a plant that is selected from among *Melilotus officinalis, Citrus limonum, Lens culinaris, Averrhoa Carambola*, and *Momordica charantia*, or a yeast that is selected from among *Candida saitoana* and *Yarrowia lipolytica*.

9. The cosmetic method according to claim 1, wherein said cutaneous cell autophagy activator is present in said composition in an amount of between 0.1 and 15% by weight relative to total weight of the composition.

10. The cosmetic composition according to claim 1, wherein said cutaneous cell autophagy activator is present in said composition in an amount of between 1% and 4% by weight relative to the total weight of the composition.

11. The cosmetic method according to claim 1, wherein said composition is in the form of a cream, gel, lotion, ointment, oil-in-water emulsion, water-in-oil emulsion or suspension.

* * * * *